(12) United States Patent
Kim et al.

(10) Patent No.: US 9,194,879 B2
(45) Date of Patent: Nov. 24, 2015

(54) SAMPLE ANALYSIS APPARATUS

(71) Applicant: SAMSUNG ELECTRONICS CO., LTD., Suwon-si (KR)

(72) Inventors: Hong Geun Kim, Suwon-si (KR); Dong Young Kim, Daegu (KR); Chung Ung Kim, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 87 days.

(21) Appl. No.: 13/728,329

(22) Filed: Dec. 27, 2012

(65) Prior Publication Data

US 2013/0164175 A1 Jun. 27, 2013

(30) Foreign Application Priority Data

Dec. 27, 2011 (KR) ........................ 10-2011-0143340

(51) Int. Cl.
*G01N 35/10* (2006.01)
*G01N 35/00* (2006.01)

(52) U.S. Cl.
CPC ...... *G01N 35/1081* (2013.01); *G01N 35/00069* (2013.01)

(58) Field of Classification Search
CPC ................................................ G01N 35/1081
See application file for complete search history.

(56) References Cited

U.S. PATENT DOCUMENTS

2009/0253130 A1* 10/2009 Yoo .................................. 435/6

FOREIGN PATENT DOCUMENTS

JP 2004-222689 A 8/2004
KR 10-2011-0079571 A 7/2011

OTHER PUBLICATIONS

Communication dated Mar. 26, 2013 issued by the Korean Intellectual Property Office in counterpart Korean Patent Application No. 10-2011-0143340.

* cited by examiner

*Primary Examiner* — Sam P Siefke
(74) *Attorney, Agent, or Firm* — Sughrue Mion, PLLC

(57) ABSTRACT

A sample analysis apparatus is provided with a structure for stopping rotation of a disc at a precise position. The sample analysis apparatus includes a disc configured to rotate on a rotation shaft and having at least one detection zone, an optical sensing apparatus configured to detect a reaction result at the at least one detection zone, at least one position determining protrusion provided on an exterior surface of the disc, a slider movably disposed to in a radial direction relative to the disc, and a stopper mounted to the slider and configured to stop rotation of the disc by blocking the at least one position determining protrusion.

18 Claims, 18 Drawing Sheets

SAMPLE ANALYSIS APPARATUS

CROSS-REFERENCE TO RELATED APPLICATION

This application claims priority from Korean Patent Application No. 10-2011-0143340, filed on Dec. 27, 2011, in the Korean Intellectual Property Office, the disclosure of which is incorporated herein by reference.

BACKGROUND

1. Field

Apparatuses consistent with exemplary embodiments relate to a sample analysis apparatus configured to stop a disc, thereby showing a detection result at a precise position.

2. Description of the Related Art

In general, a microfluidic apparatus is an apparatus which includes a microfluidic structure within which a fluid is accommodated so that various tests that include biochemical reactions may be performed. As one example of the microfluidic apparatus, a disc is provided having the microfluidic structure disposed therein, and is configured to be rotated on a rotation shaft.

The various tests that use the disc are performed by injecting a sample into the disc in order for biochemical reactions to take place, and then detecting the result of the reactions. Detection of reaction results from biochemical reactions that take place within the disc may be facilitated by optical changes.

In the related art, the reaction result is detected by a user or test administrator with the naked eye. In such cases, since the reaction result depends on the objective determination of the test administrator, the reliability of the result is reduced.

Thus, a detection apparatus configured to quantitatively detect the reaction result of a detectable reaction is used. The detection apparatus may be provided with a lighting apparatus configured to radiate light at the location of the detectable reaction, and a camera module configured to measure the amount of the light transmission or the amount of the light reflection.

As to precisely detect the reaction result, a uniform amount and intensity of light is needed to be radiated onto the detectable location, and the camera module should be disposed at a position capable of capable of measuring light being transmitted or reflected from the detectable location.

Particularly, since the disc is in rotation, the disc is needs to be stopped at a precise position in order for the camera module to precisely detect the reaction result.

SUMMARY

Exemplary embodiments provide a sample analysis apparatus provided with a structure capable of stopping a disc at a precise location.

In accordance with an aspect of an exemplary embodiment, there is provided a sample analysis apparatus including: a disc, an optical sensing apparatus, at least one position determining protrusion, a slider and a stopper. The disc may have at least one detection zone and may be configured to rotate on a rotation shaft. The optical sensing apparatus may be configured to detect a reaction result shown at the at least one detection zone. The at least one position determining protrusion may be provided on an exterior surface of the disc. The slider may be disposed so as to be movable in a radial direction relative to the disc. The stopper may be mounted on a surface of the slider, and configured to stop rotation of the disc by blocking the rotational path of at least one position determining protrusion.

The stopper may be configured to stop the rotation of the disc at a position where the optical sensing apparatus detects the at least one detection zone.

The at least one position determining protrusion may include a first position determining protrusion located a first distance from the rotational center of the disc, and a second position determining protrusion located a second distance from the rotational center of the disc.

The disc may include a first detection zone corresponding to the first position determining protrusion and a second detection zone corresponding to the second position determining protrusion.

When the stopper stops the rotation of the disc by blocking the first position determining protrusion, the first detection zone is stopped at a position where the optical sensing apparatus is able to detect the first detection zone.

When the stopper stops the rotation of the disc by blocking the second position determining protrusion, the second detection zone is stopped at a position where the optical sensing apparatus is able to detect the second detection zone.

The slider may be movably configured to move along a radial direction of the disc between the rotational center of the disc and an outer edge of the disc.

The stopper may include a securing portion configured to secure the at least one position determining protrusion.

The stopper may include a cushion member disposed on a surface that contacts the at least one position determining protrusion to prevent damage to the at least one position determining protrusion when blocking the position determining protrusion.

The stopper may include a grip unit configured to stop the position determining protrusion by pressing the position determining protrusion from opposite directions.

The slider may include a stop detection unit configured to detect whether the position determining portion is stopped by the stopper.

The stopper may be configured in a way to be moved by being pressed by the position determining protrusion. The stop detection unit may include a hinged stopper and be configured to determine, by detecting the movement of the stopper, if the position determining protrusion is stopped.

The stop detection unit may include a switch.

The slider may include a position detection unit configured in a way to detect whether the stopper is moved to a position capable of stopping the position determining protrusion.

The position detection unit may include a light emitting portion, and a light receiving portion disposed opposite one another such that the position determining protrusion will pass therebetween.

The optical sensing apparatus may be mounted to the slider.

The optical sensing apparatus may include a camera module configured to photograph the at least one detection zone.

In accordance with another exemplary aspect, a sample analysis apparatus may include a disc, an optical sensor, at least one position determining protrusion and a slider. The disc may be configured to rotate on a rotation shaft, and have at least one detection zone. The optical sensor may be configured to detect the at least one detection zone. The at least one position determining protrusion may be formed on an exterior surface of the disc. The slider may be configured to move in a radial direction relative to the disc, and to block the position determining protrusion, so that the disc is stopped at a desired position.

In accordance with an aspect of another exemplary embodiment, there is provided a sample analysis apparatus including: a disc, at least one position determining protrusion, a slider, a stopper. The disc may be configured to rotate on a rotation shaft. The at least one position determining protrusion may be provided on an outer edge of the disc and protrude away from the rotational center of the disc. The slider may be disposed to move in a radial direction relative to the disc. The stopper may be mounted on the slider, and configured to stop the rotation of the disc by blocking the position determining protrusion.

In accordance with an aspect of another exemplary embodiment, there is provided a sample analysis apparatus including: a disc including at least one position determining groove, a slider and a stopper. The disc may be configured to rotate on a rotation shaft. The at least one position determining groove may be recessed into an outer edge of the disc and extend radially inwardly. The slider may be disposed to move in a radial direction relative to the disc. The stopper may be mounted on the slider, and configured to be inserted into the position determining groove to stop the rotation of the disc.

In accordance with an aspect of another exemplary embodiment, there is provided a sample analysis apparatus including: a disc including at least one position determining hole, a slider and a stopper. The disc may be configured to rotate on a rotation shaft. The at least one position determining hole may be formed through the disc or at least a portion of the surface of the disc, while being arranged in a circumferential direction of the disc. The slider may be disposed to move in a radial direction relative to the disc. The stopper may be mounted on the slider, and configured to be inserted in the position determining hole to stop the rotation of the disc.

BRIEF DESCRIPTION OF THE DRAWINGS

The above and/or other aspects will become apparent and more readily appreciated from the following description of exemplary embodiments, taken in conjunction with the accompanying drawings of which.

DETAILED DESCRIPTION

Figure 1:
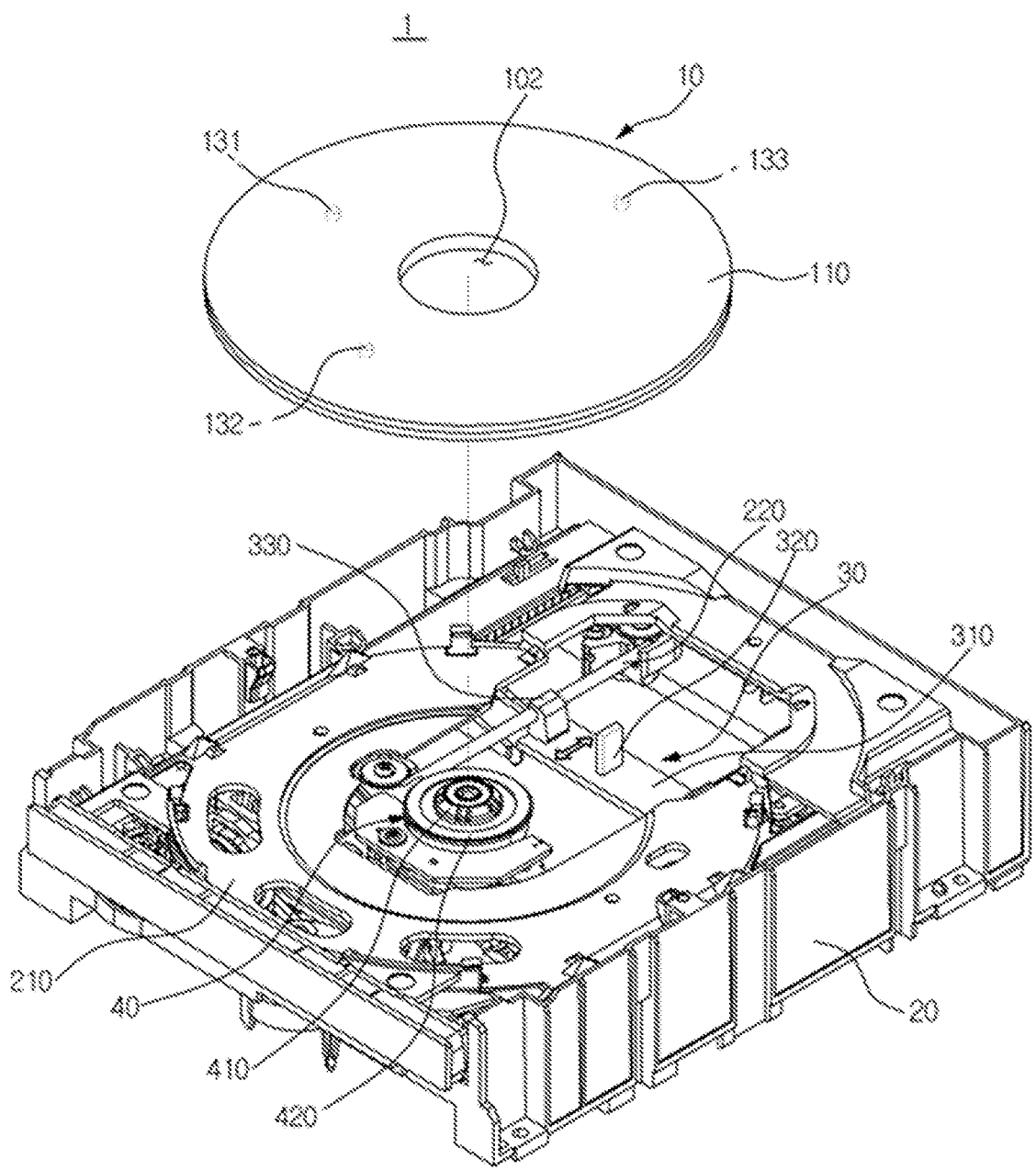
FIG. 1 is a perspective view illustrating a configuration of a sample analysis apparatus in accordance with a first exemplary embodiment.

Exemplary embodiments will now be described in detail with reference to the accompanying drawings, wherein like reference numerals refer to like elements throughout.

FIG. 1 is a perspective view illustrating a structure of a sample analysis apparatus in accordance with a first exemplary embodiment.

As illustrated in FIG. 1, the sample analysis apparatus 1 includes a disc 10 within which a reaction result is produced as a sample is reacted, and a body 20 forming an exterior structure.

The disc 10 may include a platform 110 having an exterior upper surface, at least one chamber disposed within the platform 110 so that a fluid may be accommodated therein, and at least one channel through which the fluid may flow. At a central portion of the disc 10, a central hole 11 having a predetermined diameter is formed so that a rotation apparatus 40 configured to rotate the disc 10 may be coupled to the central hole 11. Thus, the disc 10 is formed in the shape of a ring as a whole.

Within the body 20, there is formed a settling surface 210 configured to allow the disc 10 to be settled at the body 20. The settling surface 210 is formed in a shape that corresponds to the shape of the disc 10, so that the disc 10 may be stably supported.

Within the body 20, the rotation apparatus 40 is mounted. The rotation apparatus 40 includes a motor 420 configured to generate the rotation force that is delivered to the disc 10. At an upper portion of the motor 420, there is provided a fixing portion 410, which is configured to fix and position the disc 10 while being inserted into a central hole 102 of the disc 10 and protruded toward an upper surface thereof.

Within the body 20, a slider 30 is mounted such that the body 20 may be moved along a radial direction of the settling surface 210. The slider 30 is coupled to a bar-shaped guide member 220, and moves along the guide member 220 in a radial direction of the settling surface 210.

The rotation apparatus 40 is disposed at a central portion of the settling surface 210. Because the slider 30 is disposed to be movable from an outer side of the settling surface 210 to a central portion of the settling surface 210 in a radial direction, the settling surface 210, as a whole, is formed in the shape of a ring having an open side.

Figure 2:
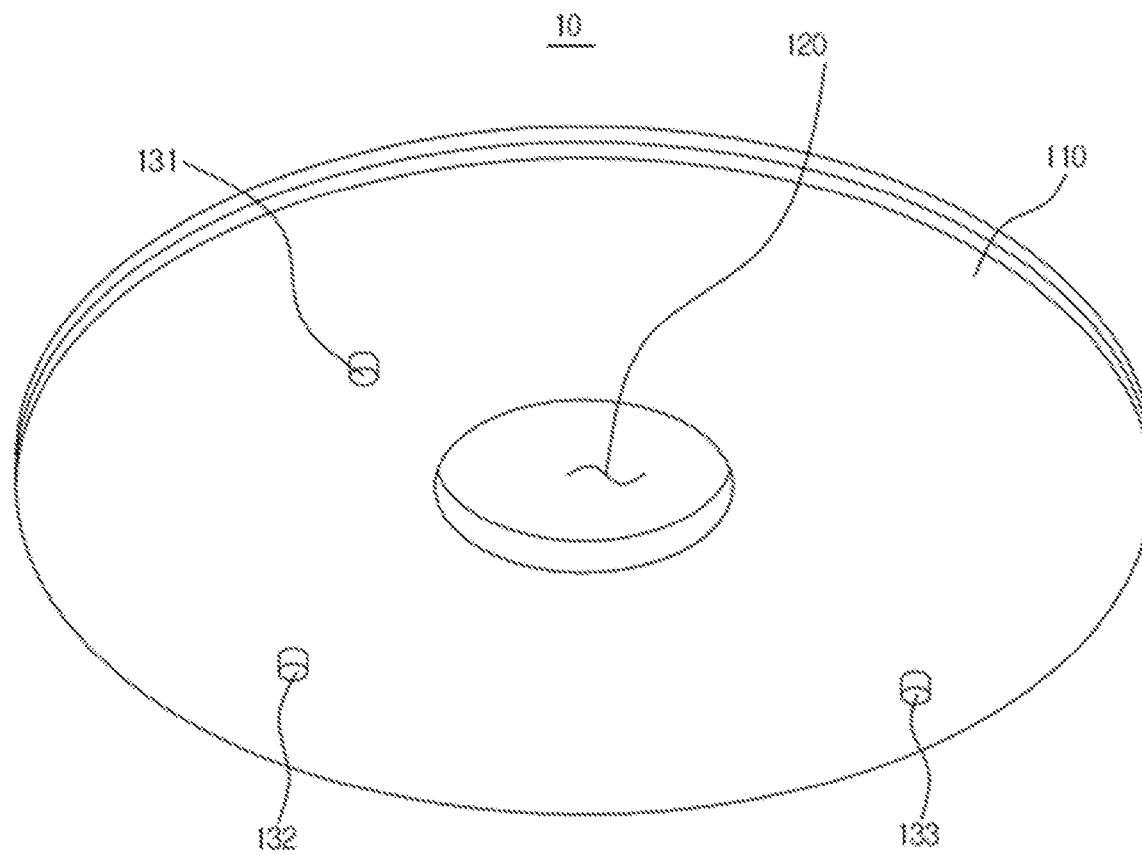
FIG. 2 is a perspective view illustrating the disc of FIG. 1.
Figure 3:
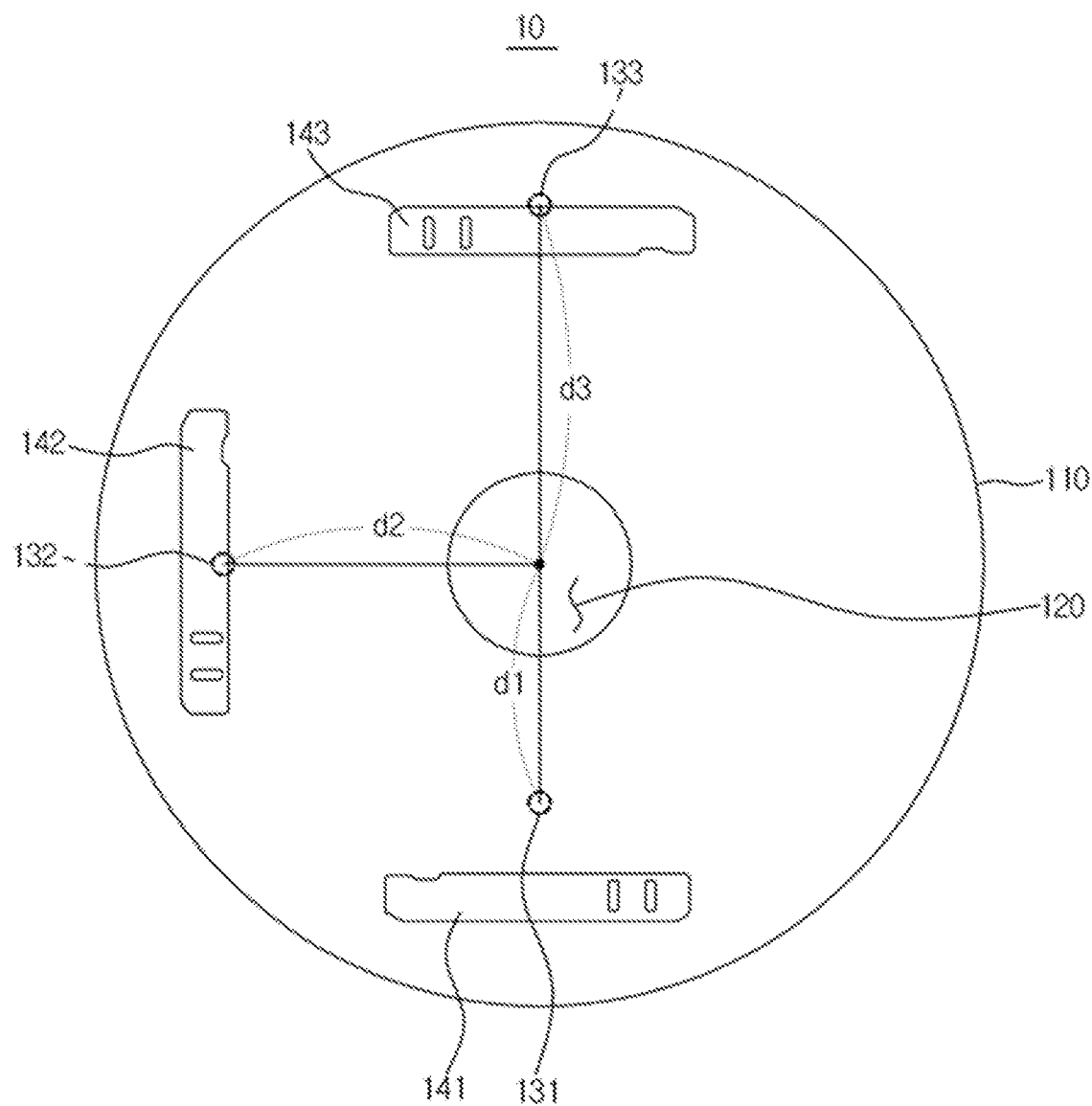
FIG. 3 is a top view illustrating the disc of FIG. 1.

FIG. 2 is a perspective view illustrating the disc shown in FIG. 1, and FIG. 3 is a drawing of a top view of the disc shown in FIG. 1. In order to show the positional relationship between a detectable location and a position determining protrusion in FIG. 3, other components such as a chamber and a channel are omitted.

As illustrated in FIG. 2 and FIG. 3, the platform 110, having the shape of a ring, forms an exterior surface of the disc 10. The platform 110 may be made of a plastic material, such as acrylic or polydimethylsiloxane (PDMS), that is biologically non-volatile. However, the material of the platform 110 is not limited thereto, and it may be sufficient to be formed from any material having properties such as chemical and biological stability, optical transparency, and mechanical processability.

The platform 110 may be composed of several layers. At the mating surfaces where a first panel and second panel meet, intaglio structures corresponding to one or more chambers or channels may be formed. By coupling the intaglio structures, such chambers and channels may be provided within the platform 110. For example, the platform 110 may be a structure composed of an upper panel, and a lower panel that is attached to the upper panel, or may be a structure that is provided with a compartment panel disposed between the upper and lower panels. Such compartment panel may be configured to define the chamber at which a fluid may be accommodated, and the channel through which the fluid may flow. Coupling of the upper panel and the lower panel may be accomplished by any of various methods such as through use of adhesive, double-sided adhesive tape, ultrasonic wave welding, or laser welding.

The disc 10 includes first, second and third detectable locations (or detection zones) 141, 142, and 143 provided therein to allow for detection a reaction result from outside the disc 10. The detection zones 141, 142, and 143 may each include a chamber within which is accommodated reaction result material that is generated when a sample is reacted with a reagent. The chamber may further include a reagent cartridge that is disposed in a way so as to allow the reagent to react with a sample.

In this exemplary embodiment, a total of three detection zones 141, 142, and 143 are provided. Formed on an exterior surface of the platform 110, and corresponding to each of the detection zones 141, 142, and 143 is a position determining protrusion 130. In this exemplary embodiment, a total of three position determining protrusions 131, 132, and 133, corresponding to the number of the detection zones 141, 142, and 143, are provided. As should be understood, the number of the position determining protrusions 132, 132, and 133 and the number of the detection domains 141, 142, and 143 each are not limited to three, and therefore may be less than or greater than three.

As shown in FIG. 3, each of the position determining protrusions 131, 132, and 133 is positioned at a different distance from the center 120 of the platform 110. The first position determining protrusion 131 is positioned at a first distance 'd1', the second position determining protrusion 132 is positioned at a second distance 'd2', and the third position determining protrusion 133 is positioned at a third distance 'd3'.

Figure 4:
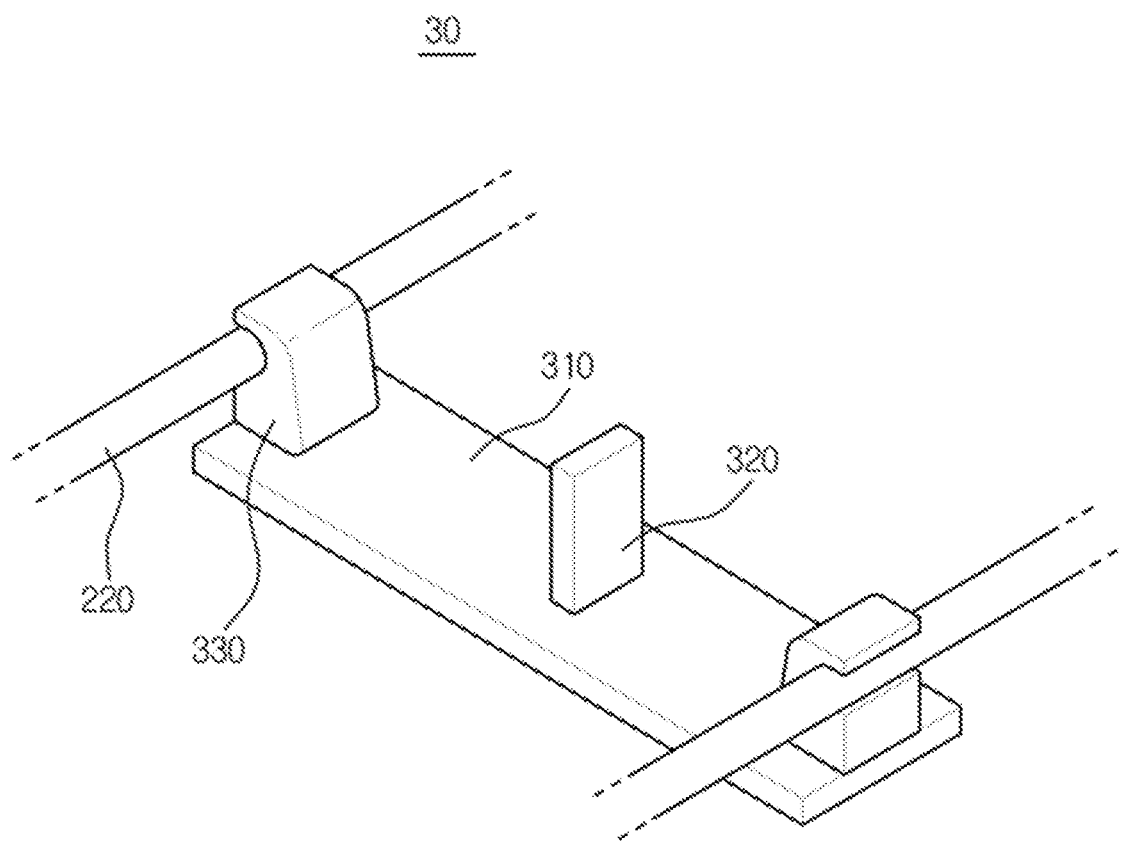
FIG. 4 is a drawing illustrating an enlarged view of the slider of FIG. 1.

FIG. 4 is a drawing illustrating an enlarged view of the slider shown in of FIG. 1.

As illustrated in FIG. 4, the slider 30 includes a plate 310, a stopper 320 formed on an upper surface of the plate 310 and protruding toward an upper side of the body 20, and a supporting portion 330 formed at both of the side edges of the plate 310, also protruding toward an upper side of the body 20.

The stopper 320 is configured to stop the rotation of the disc 10 by blocking and contacting the position determining protrusions 131, 132, and 133.

The supporting portion 330 is slidingly mounted to a guide member 220, so as to enable the slider 30 to be movable along the guide member 220.

Figure 5:
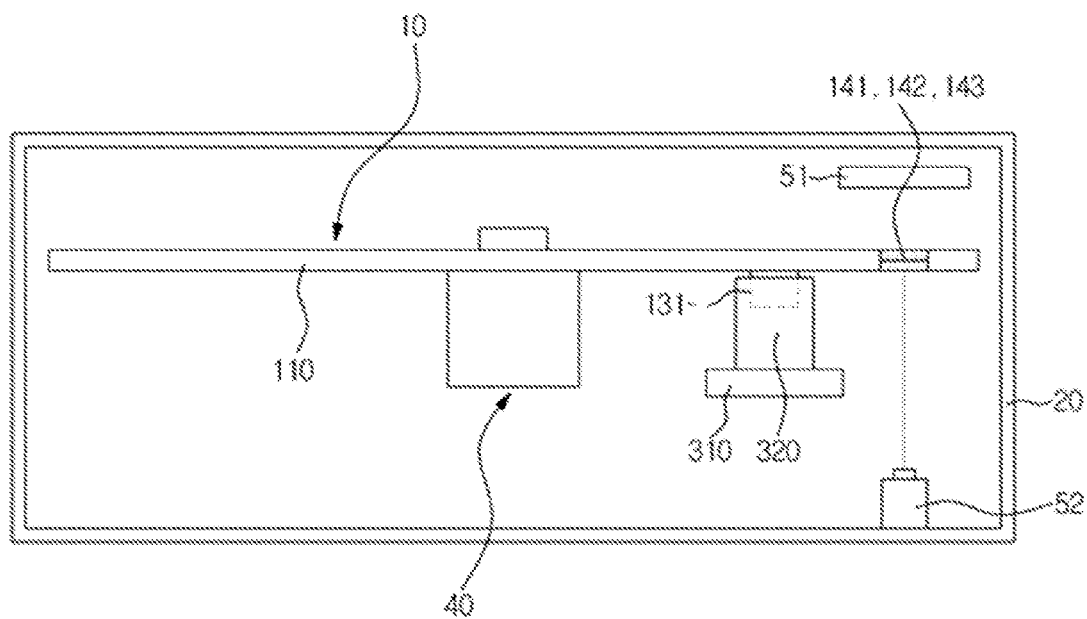
FIG. 5 is a cross-sectional view illustrating a configuration of the sample analysis apparatus of FIG. 1.

FIG. 5 is a cross-sectional view illustrating a structure of the sample analysis apparatus shown in FIG. 1. In order to illustrate the structure of the optical sensing apparatus, only a portion of the structure is illustrated in FIG. 5.

In an exemplary embodiment, a reaction result may be detectable using a method that includes radiating light of a particular wavelength onto the detection zones 141, 142, and 143, and measuring any change in wavelength of the light that penetrates through the detection zones 141, 142, and 143. In another exemplary embodiment, detection of a reaction result may be accomplished using a method that includes radiating light at the detection zones 141, 142, and 143, and photographing an image of the detection zones 141, 142, and 143. However, it should be understood that such methods of detection are not limited thereto, and various methods, such as radiating a light at the detection zones 141, 142, and 143, detecting light penetrating the detection zones 141, 142, and 143, or receiving light being reflected from the detection zones 141, 142, and 143, may be used.

A lighting apparatus 51 may be disposed at above of an upper surface of the disc 10, while being spaced apart from the upper surface of the disc 10 by a predetermined distance to radiate light at the detection zones 141, 142, and 143. However, the lighting apparatus 51 may also be disposed under a lower surface of the disc while being spaced apart from the lower surface of the disc 10.

As such, the lighting apparatus 51 is disposed to face the detection zones 141, 142, and 143, and directly radiates light onto the detection zones 141, 142, and 143.

An optical sensing apparatus 52 is disposed at an opposite side of the lighting apparatus 51, while having the detection zones 141, 142, and 143 therebetween, in order to receive the light being penetrated through the detection domains 141, 142, and 143.

The optical sensing apparatus 52 may include a camera module configured to photograph images of the detection zones 141, 142, and 143. By photographing images of the detection zones 141, 142, and 143, the camera module is capable of recording the reaction results at the detection zones 141, 142, and 143 in the form of data.

The camera module may include an image photographing apparatus having a method of a CMOS (Complementary Metal-Oxide Semiconductor) or a method of a CCD (Charge-Coupled Device).

First, a sample is injected into the disc 10. The sample may be a biomaterial such as blood, saliva, or urine. Within the disc 10, materials such as reagents that react to particular components of the sample are provided. While the disc 10 is rotated by the rotation apparatus 40, the sample and the reagent are reacted with each other within the disc 10, and the reaction result is shown at the detection zones 141, 142, and 143. In order to detect the reaction result, the lighting apparatus 51 radiates light onto the detection zones 141, 142, and 143, and the optical sensing apparatus 52 receives the light that penetrates through the detection zones 141, 142, and 143.

The method of obtaining data by using the light that is received at the optical sensing apparatus 52 may vary. For example, the method may include comparing the wavelength of the light that is being radiated from the lighting apparatus 51, with the wavelength of the light that is being received at the optical sensing apparatus 52 after penetrating the detection zones 141, 142, and 143. By comparing the wavelengths of the lights, it may be determined whether the reagent actually reacted to the particular component of the sample, and whether the reaction result is expressed at the detection zones 141, 142, and 143. And if it is found that the reaction result is expressed at the detection zones 141, 142, and 143, the degree of the reaction may also be detected by calculating the change in wavelength.

In exemplary embodiments where the optical sensing apparatus 52 is a camera module, images of the detection zones 141, 142, and 143 are photographed. The photographed reaction results may show optical changes, such as color or density changes of the reaction material positioned at the detection zones 141, 142, and 143. Any recorded changes in color or density of the detection zones 141, 142, and 143 may be provided in the form of data. Through analysis of the images after photographing, the reaction result may be quantitatively interpreted.

In the sample analysis apparatus 1 provided herein, the lighting apparatus 51 and the optical sensing apparatus 52 may be positioned at opposite positions to each other while having the detection zones 141, 142, and 143 therebetween. However, the lighting apparatus 51 and the optical sensing apparatus 52 may be disposed on the same side of the disc 10 in order to receive the light being reflected from the disc 10.

Although not illustrated in the drawings, in accordance with another exemplary embodiment, the optical sensing apparatus 52 may be mounted to the slider 30.

Figure 6:
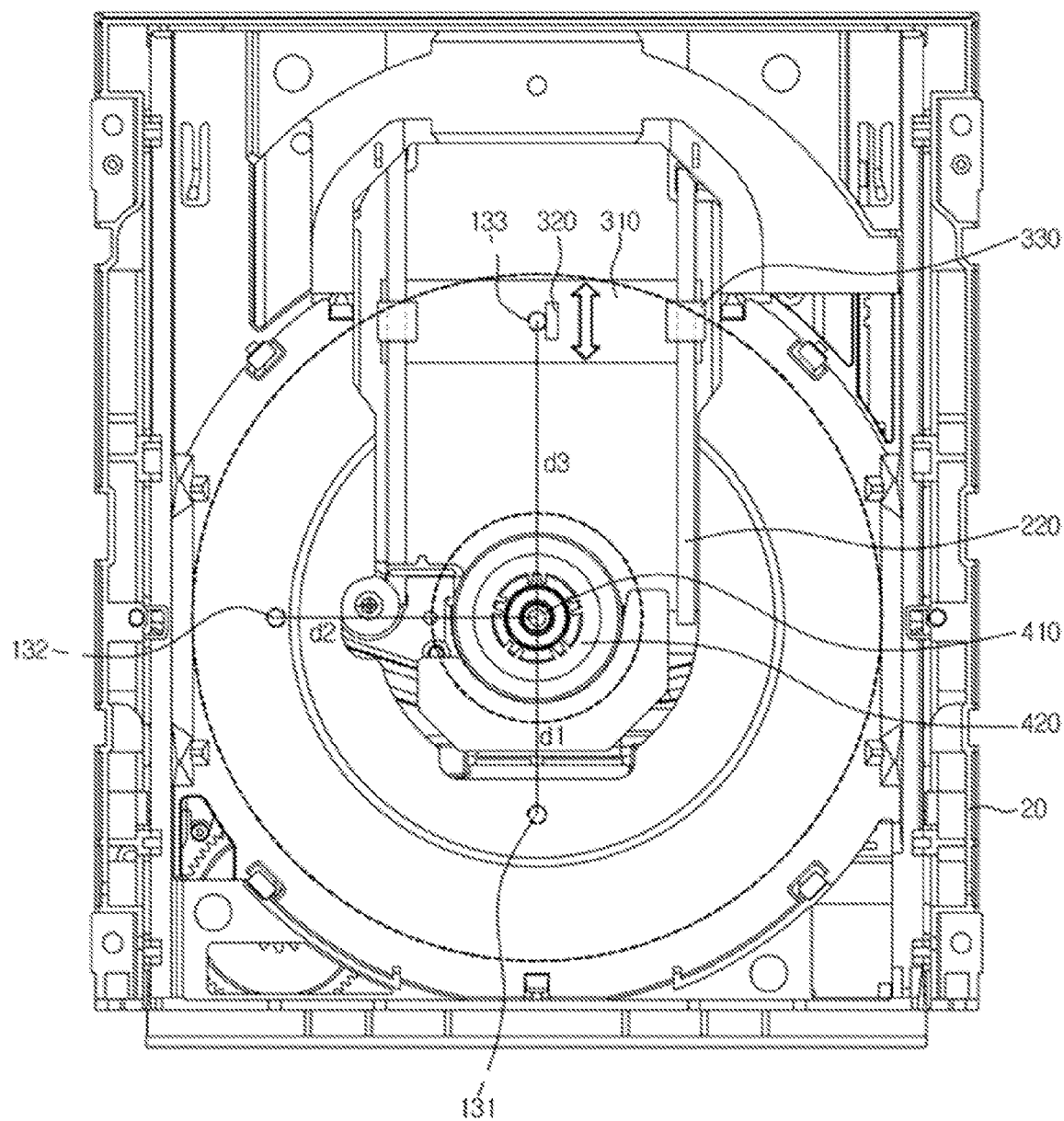
FIGS. 6 to 8 are drawings illustrating motion of the sample analysis apparatus of FIG. 1.
Figure 7:
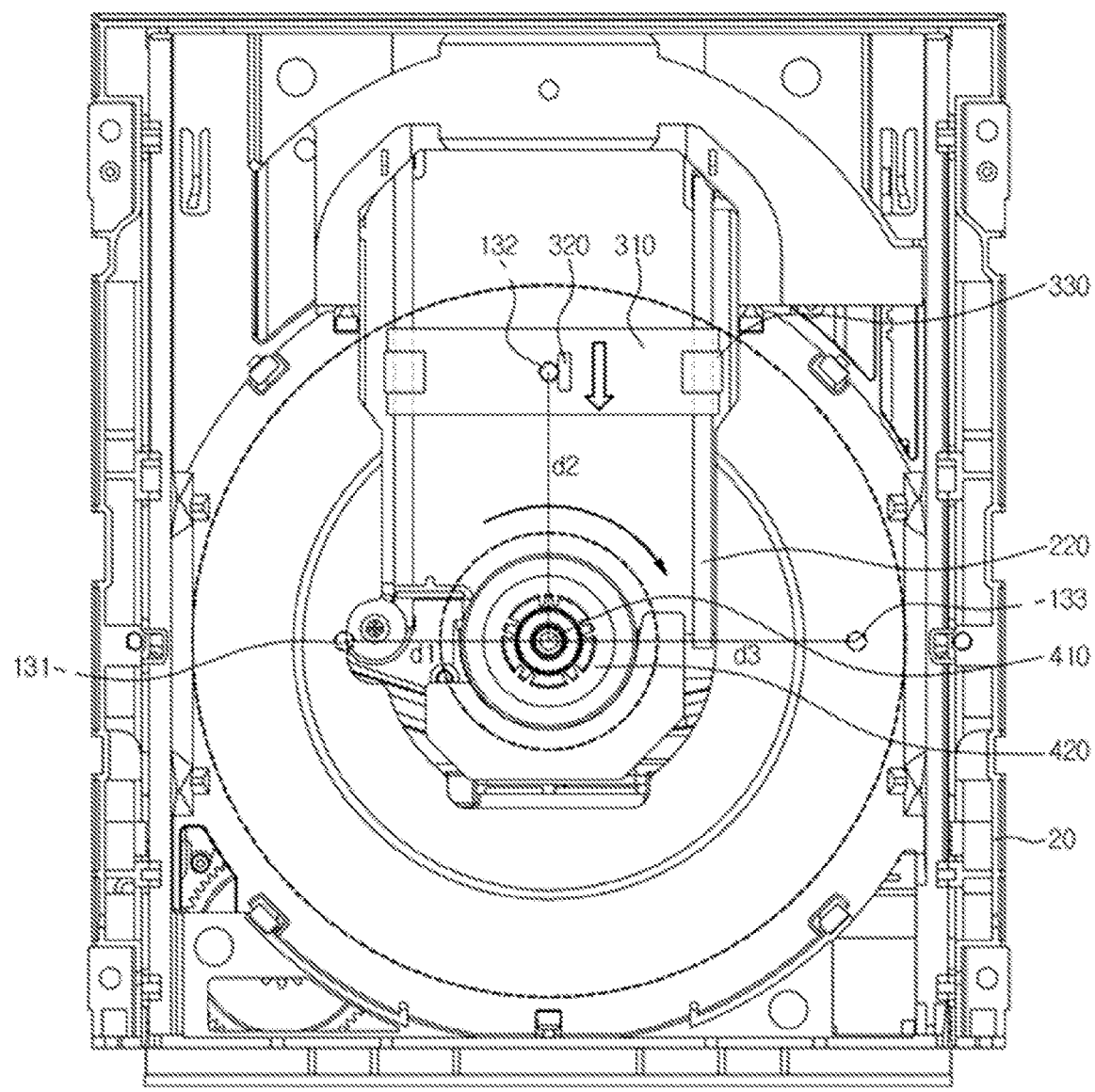
Figure 8:
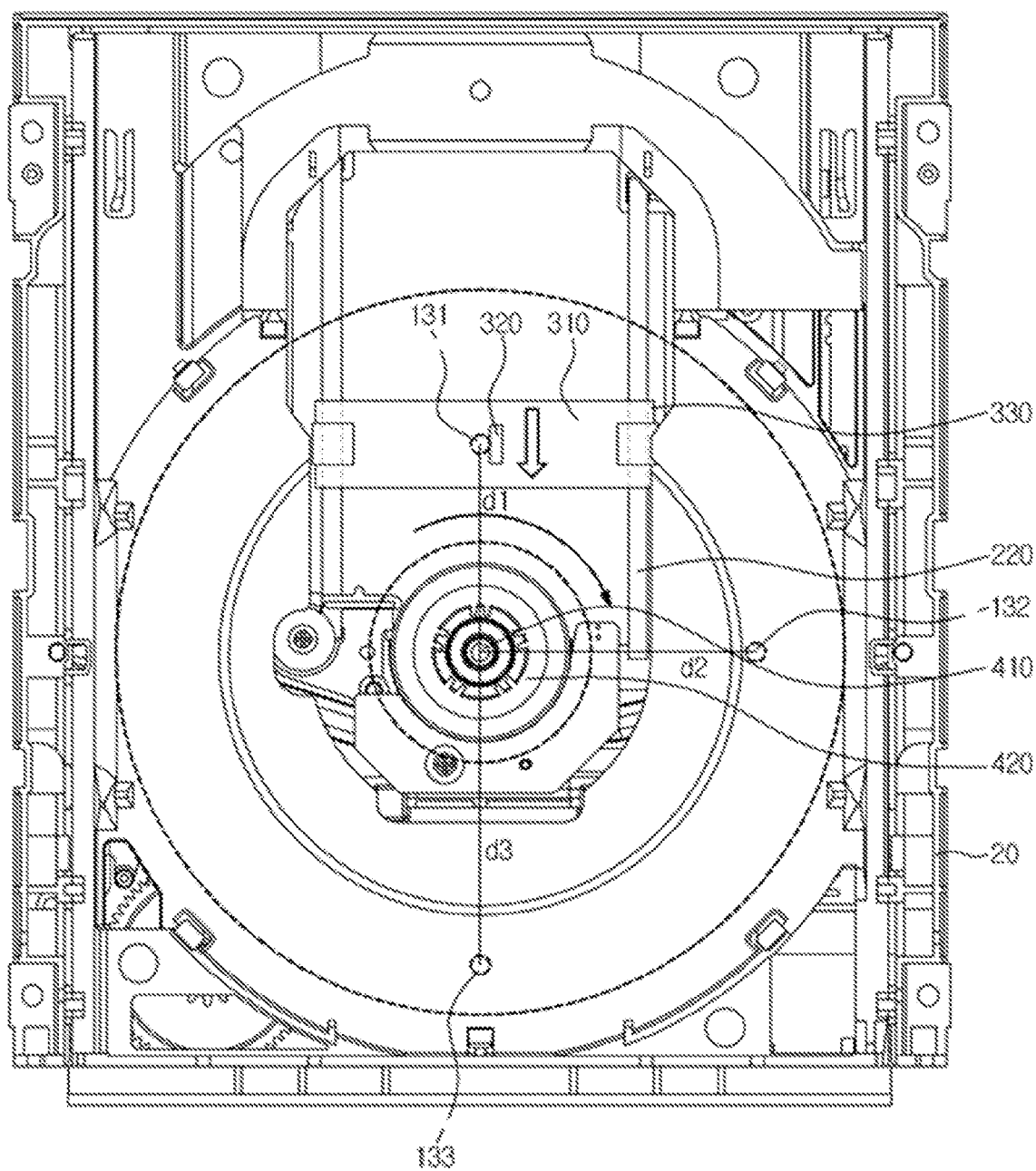

FIGS. 6 to 8 are drawings illustrating motion of the sample analysis apparatus shown in FIG. 1.

FIG. 6 is a drawing illustrating the stopper 320 blocking the third position determining protrusion 133 to stop rotation of the disc 10, such that the reaction result within the third detection zone 143 may be detected by the optical sensing apparatus 52 (refer to FIG. 5).

From an initial position, the slider 30 moves to a position, consistent with the third distance 'd3' from the rotation center 120 of the disc 10. As the slider 30 moves into position, the rotational path of the third position determining protrusion 133 is blocked by the stopper 320. Thus, the disc 10 is also stopped.

Here, the position at which the disc 10 is stopped is the position at which the third detection zone 143 is located between the optical sensing apparatus 52 and the lighting apparatus 51 (refer to FIG. 5). Thus, as described above, the optical sensing apparatus 52 detects the detection result of the third detection zone 143.

FIG. 7 is a drawing illustrating the stopper 320 blocking the second position determining protrusion 132 to stop rotation of the disc 10, so that the reaction result within the second detection zone 142 may be detected by the optical sensing apparatus 52 (refer to FIG. 5).

FIG. 8 is a drawing illustrating the stopper 320 blocking the first position determining protrusion 131 to stop rotation of the disc 10, so that the reaction result of the first detection zone 141 may be detected by the optical sensing apparatus 52 (refer to FIG. 5).

As described above, since the first position determining protrusion 131, the second position determining protrusion 132, and the third position determining protrusion 133 are disposed at a different distances from the center 120 of the disc 10, the slider 30 may be moved so as to block rotation of any one of the position determining protrusions 131, 132, and 133. As such, when the disc 10 is rotated, the slider 30 will stop only the desired position determining protrusion without blocking the other position determining protrusions disposed on the external surface of the disc.

FIGS. 9 to 12 are drawings illustrating another exemplary embodiment of a stopper.

Figure 9:
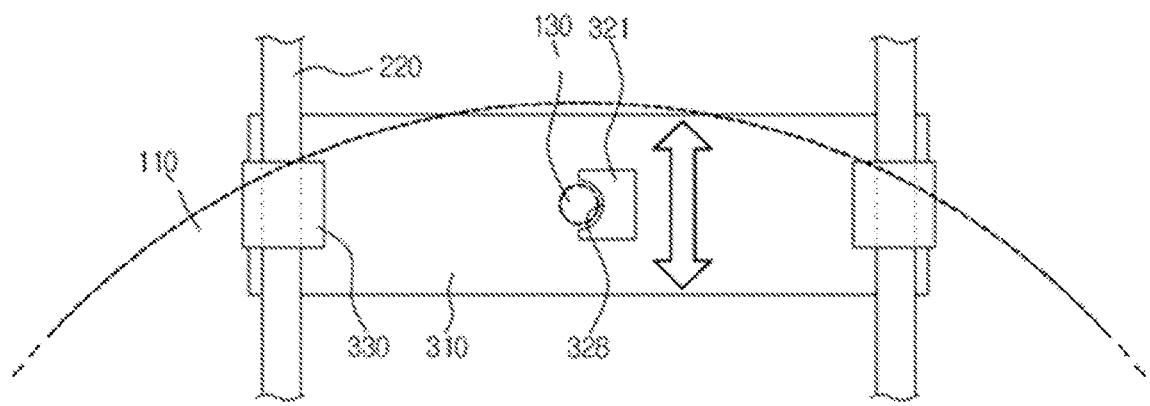
FIGS. 9 to 12 are drawings illustrating another exemplary embodiment of a stopper.

A stopper 321, as illustrated in FIG. 9, is provided with a securing portion 328 formed in accordance with the position determining protrusion 130, so that the position determining protrusion 130 is stopped and secured by the securing portion 328. The securing portion 328 is formed with the shape that corresponds to the shape of the position determining protrusion 130.

In the exemplary embodiment, the securing portion 328 is formed in the shape of a semicircle, which corresponds to the circular-shape of the position determining protrusion 130 in order to stably stop the position determining protrusion.

Figure 10:
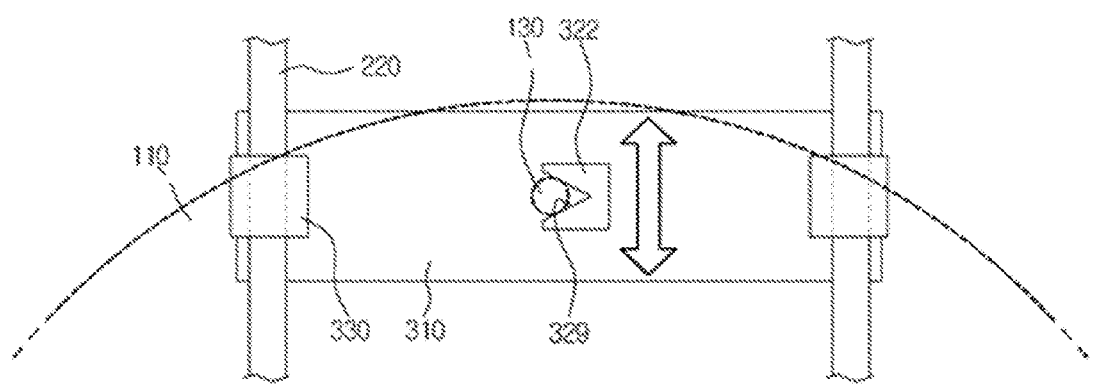

A stopper 322, as illustrated in FIG. 10, is also provided with a securing portion 329 formed in accordance with the position determining protrusion 130, such that the position determining protrusion 130 may be settled at the securing portion 329. The securing portion 329 in this exemplary embodiment is formed in the shape of a triangle.

Figure 11:
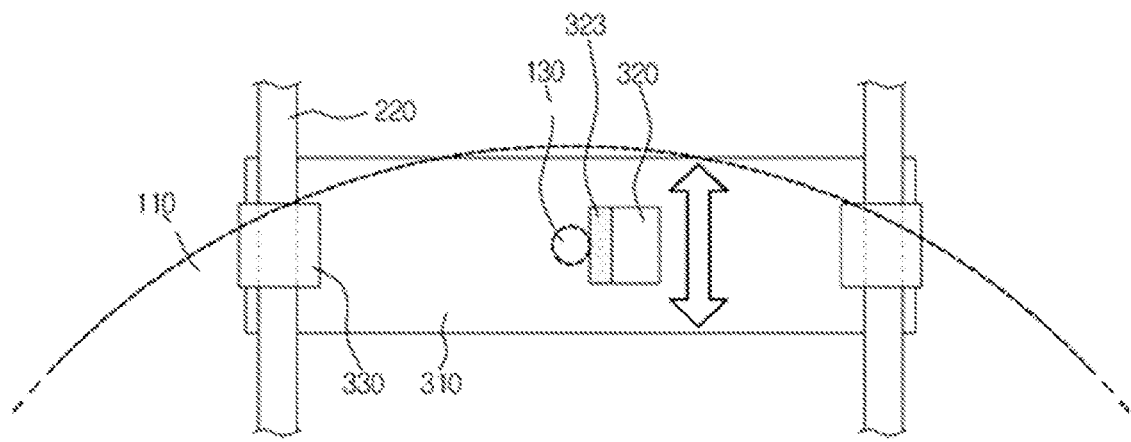

The stopper 320 illustrated in FIG. 11 is provided with a cushion member 323 mounted at a front surface of the stopper 320.

The cushion member 323 is configured to absorb the impact that is generated at the time when the stopper 320 stops the position determining protrusion 130. Thus, incorporation of the cushion member 323 may prevent damage to the position determining protrusion 130 and/or the stopper 320 due to the impact from stopping rotation of the disc 10.

It should be understood that any shape of the stopper may be used provided that the stopper stops the rotation of the disc 10 by blocking the position determining protrusion 130, thereby positioning the respective detection zone at a desired location.

Figure 12:
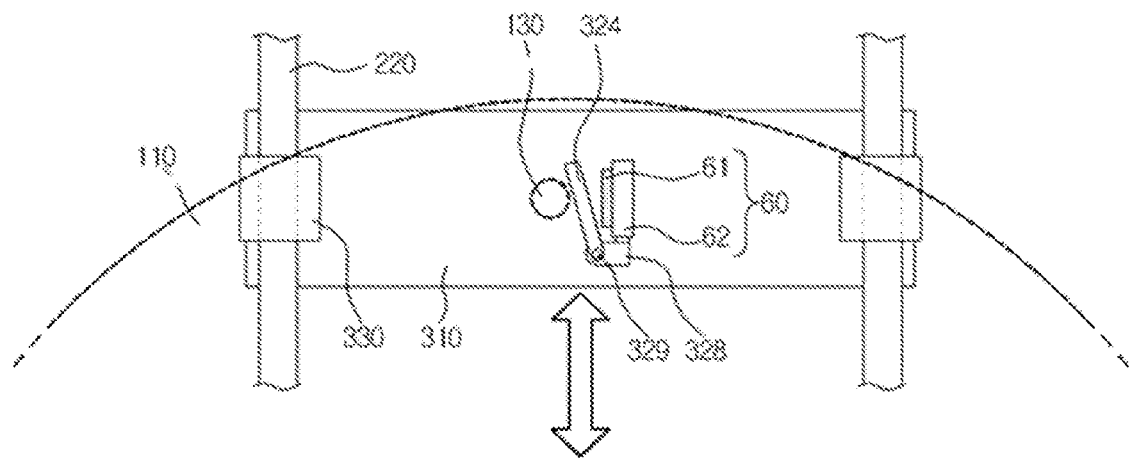

FIG. 12 is a drawing illustrating a slider of a sample analysis apparatus in accordance with another exemplary embodiment.

As illustrated in FIG. 12, the slider 30 includes a stopper 324 and a stop detection unit 60.

The stop detection unit 60 determines whether the disc 10 is stopped, by detecting contact between the position determining protrusion 130 and the stopper 324.

An end portion of one side of the stopper 324 is rotatably mounted to a shaft 329 that is coupled to a supporting body 328. Thus, the stopper 324 is rotated by a predetermined angle while having the shaft 329 as a center of rotation.

Behind the stopper 324, the stop detection unit 60 is disposed. The stop detection unit 60 includes a switch body 62 and a switch 61.

As the position determining protrusion 130 rotates with the disc 10 and makes contact with the stopper 324, the position determining protrusion 130 presses the stopper 324, thereby rotating the stopper toward a rear direction. The pressed stopper 324 therefore presses the switch 61 while rotating. When the switch 61 is pressed, a control portion (not shown) detects that the position determining protrusion 130 is blocked by the stopper 324, and may also determine that rotation of the disc 10 is stopped.

In the exemplary embodiment, while the stop detection unit 60 is illustrated to include a switch, any apparatus capable of detecting that contact is made between the stopper 324 and the position determining protrusion 130 is included in the embodiment.

Figure 13:
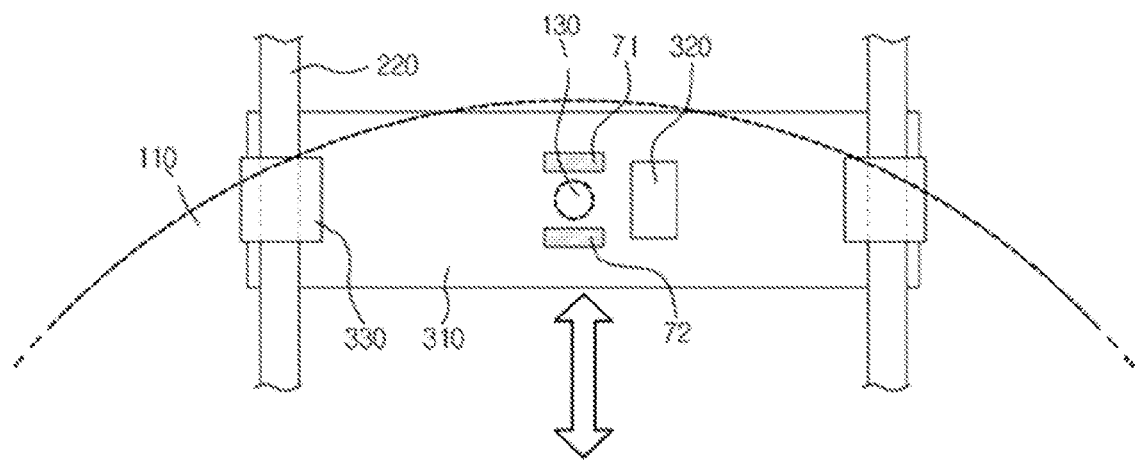
FIG. 13 is a drawing illustrating a slider of a sample analysis apparatus in accordance with another exemplary embodiment.

FIG. 13 is a drawing illustrating a slider of a sample analysis apparatus in accordance with another exemplary embodiment.

As illustrated in FIG. 13, the slider 30 includes the stopper 320 and a position determining unit.

The position determining unit may include an optical sensor composed of a light emitting portion 71, and a light receiving portion 72 configured to receive the light emitted from the light emitting portion 71. The light emitting portion 71 and the light receiving portion 72 are disposed at a predetermined distance from each other.

As the slider 30 moves to a precise position to block the rotational path of the position determining protrusion 130, the position determining protrusion 130 passes between the light emitting portion 71 and the light receiving portion 72. Thus, a control unit (not shown) may determine that the slider 30 is moved to the precise position by detecting when the light being emitted from the light emitting portion 71 is not being received at the light receiving portion 72.

On the contrary, if the control unit (not shown) does not detect the presence of position determining protrusion 130 as it passes between the light emitting portion 71 and the light receiving portion 72, even though the slider 30 is moved to block the position determining protrusion 130, then the control unit (not shown) determines that the slider 30 is not positioned at the precise position and moves the slider 30 again.

Thus, the position determining unit may be used to detect whether the slider 30 is precisely moved to a desired position.

In the exemplary embodiment, while an optical sensor is used for the position determining portion, any other apparatus capable of detecting a position of the position determining protrusion 130 may be included therein.

Figure 14:
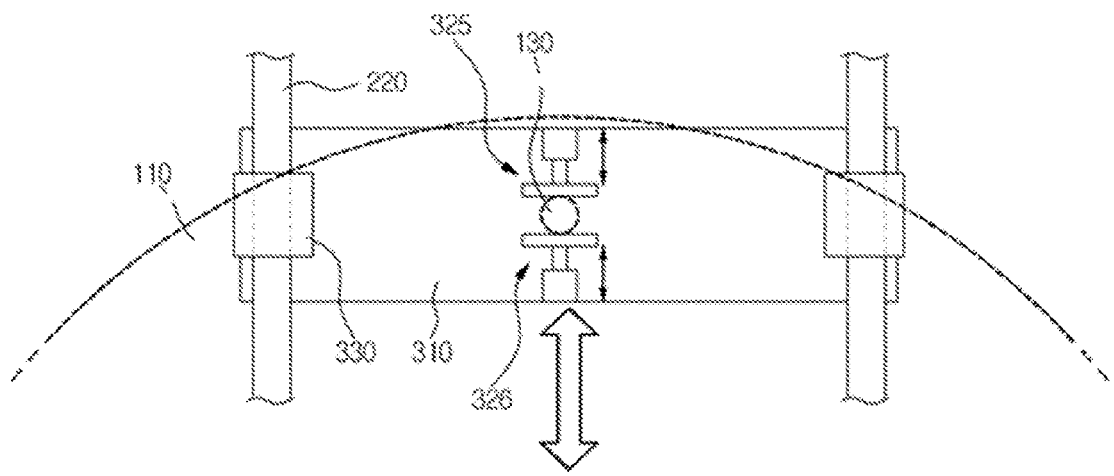
FIG. 14 is a drawing illustrating a slider of a sample analysis apparatus in accordance with still another exemplary embodiment.

FIG. 14 is a drawing illustrating a slider of a sample analysis in accordance with still another exemplary embodiment.

As illustrated in FIG. 14, the slider 30 may include a plate 310, and grip units 325 and 326 that are mounted to the plate 310.

The grip units 325 and 326 are disposed in a way such that the two grip units 325 and 326 are facing each other. Each of the grip units 325 and 326 are disposed in such a way as to move forward/backward along a radial direction of the disc 10 relative to the center of rotation 120 thereof. That is, as the grip units 325 and 326 are moved forward/backward the distance separating the two grip units 325 and 326 becomes narrower or wider.

Thus, the grip units 325 and 326 may be used to stop the rotation of the disc 10 by holding the position determining protrusion 130.

Figure 15:
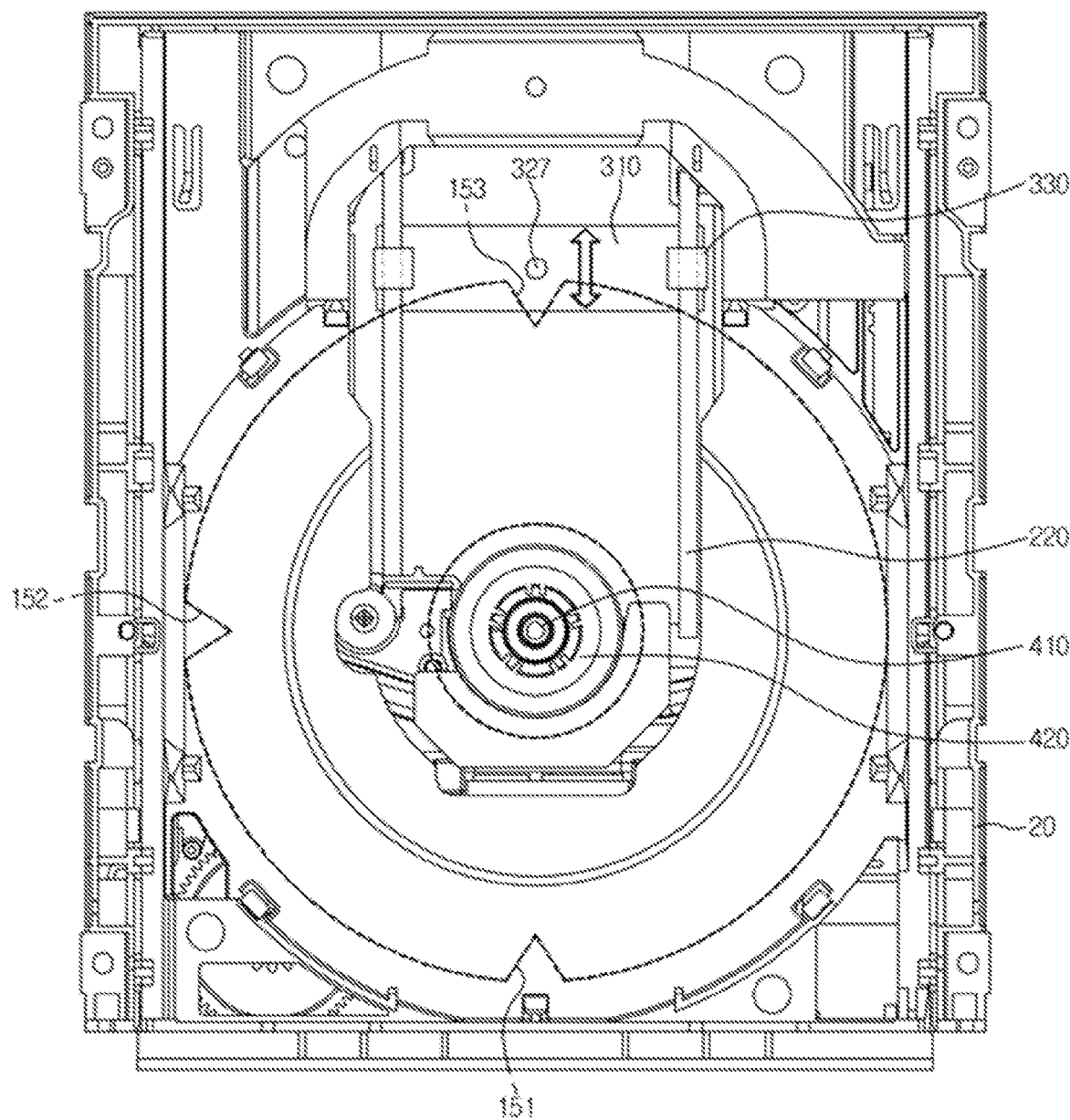
FIG. 15 is a drawing illustrating the configuration of a sample analysis apparatus in accordance with the second exemplary embodiment.

FIG. 15 is a drawing illustrating a sample analysis apparatus in accordance with another exemplary embodiment.

The description will be provided based on the differences from the other exemplary embodiments discussed above.

As illustrated in FIG. 15, the sample analysis apparatus includes a disc 10 within which a reaction result is shown, and a body 20 forming an exterior structure of the sample analysis apparatus.

Disposed on the rim of the disc 10 are one or more position determining grooves 151, 152, and 153. In this exemplary embodiment, a total of three position determining grooves 151, 152, and 153 are formed. However, any number of position determining grooves 151, 152, and 153 may be used, as long as the number of the position determining grooves is same as the number of the detection zones that are formed within the disc 10.

The position determining grooves 151, 152, and 153 are formed at positions that correspond to at least one detection zone. Thus, when a detection zone accommodating a sample to be detected needs to be stopped, a stopper 327 disposed on the slider 30 is inserted into the appropriate position determining groove to stop the disc 10.

Thus, when the stopper 327 is inserted into the appropriate position determining groove, the disc 10 is stopped at a desired position.

Figure 16:
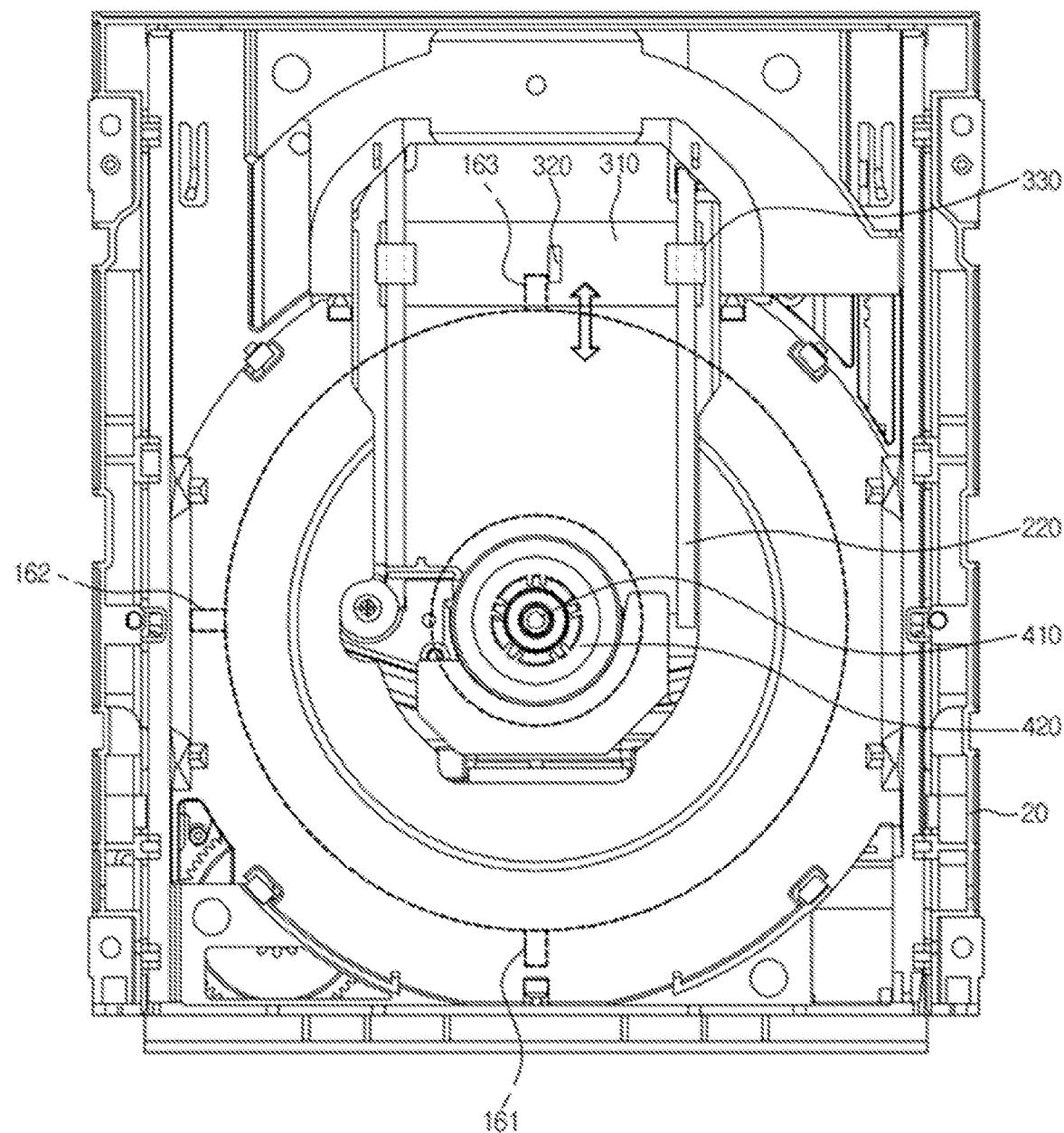
FIG. 16 is a drawing illustrating the configuration of a sample analysis apparatus in accordance with the third exemplary embodiment.

FIG. 16 is a drawing illustrating a sample analysis apparatus in accordance with another exemplary embodiment.

As illustrated in FIG. 16, the sample analysis apparatus includes a disc 10 within which a reaction result is shown, and a body 20 forming an exterior structure of the sample analysis apparatus.

In the exemplary embodiment, position determining protrusions 161, 162, and 163 are formed on the rim of the disc 10 and protrude away from the center of rotation 120 of the disc 10 in a radial direction. In the exemplary embodiment, a total of three position determining protrusions 161, 162, and 163 are formed, but any number of position determining protrusions may be used as long as the number of the position determining protrusions 161, 162, and 163 is same as the number of the detection zones that are formed within the disc 10.

The position determining protrusions 161, 162, and 163 are formed at positions corresponding to at least one detection zone. Thus, when a detection zone needs to be stopped, the stopper 320 disposed on the slider 30 blocks the corresponding position determining protrusion to stop the disc 10.

Figure 17:
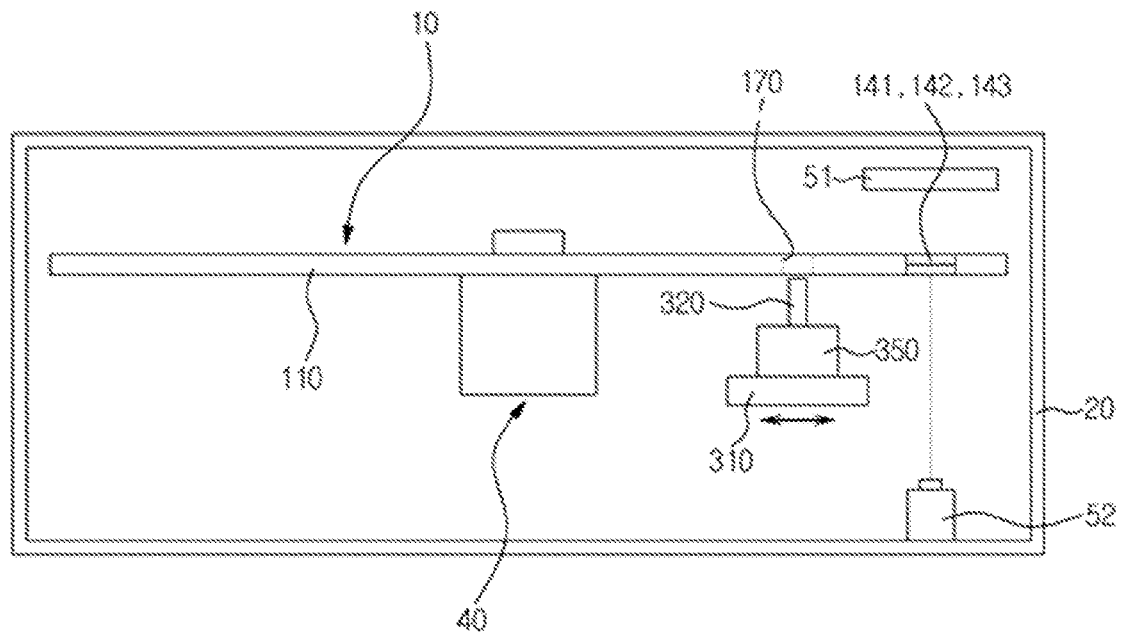
FIGS. 17 to 18 are cross-sectional views illustrating a configuration of a sample analysis apparatus in accordance with the fourth exemplary embodiment.
Figure 18:
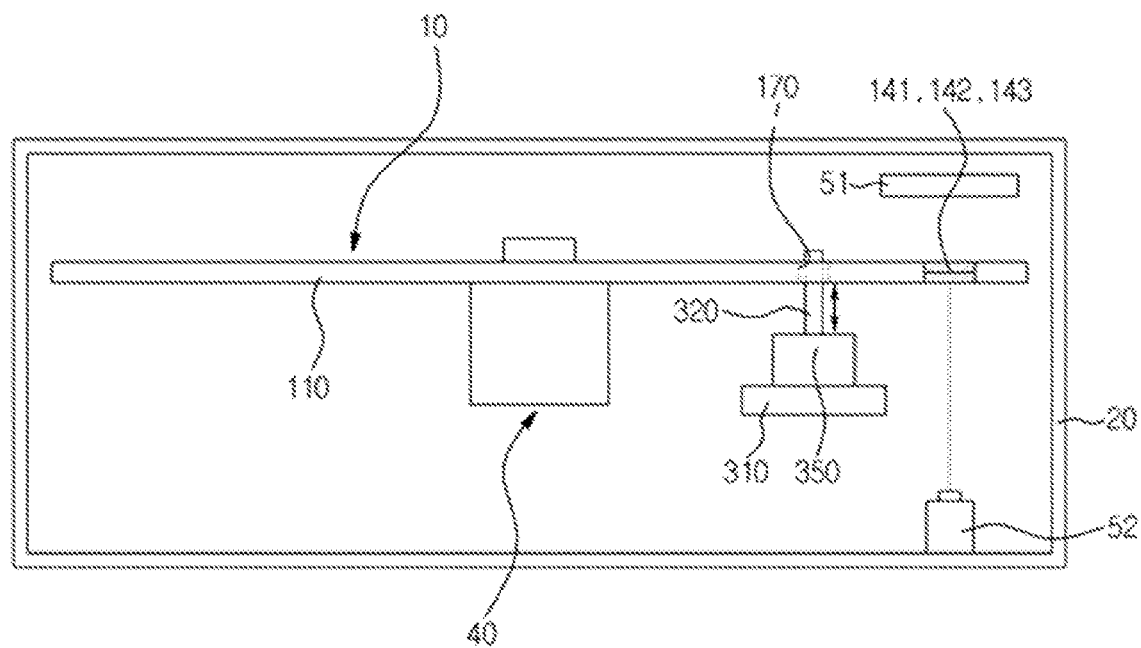

FIGS. 17 to 18 are cross-sectional views illustrating the structure of a sample analysis apparatus in accordance with an exemplary embodiment.

As above, the description of this exemplary embodiment will be provided based on the differences from the other exemplary embodiments described above.

As illustrated in FIGS. 17 to 18, the sample analysis apparatus includes a disc 10 and a body 20.

The disc 10 is provided with the ring-shaped platform 110 forming the exterior surface of the disc 10. Within the platform 110, a detection zone is formed, and a position determining hole 170 is formed through a portion of the platform 110 corresponding to the detection zone.

The slider 30 includes a plate 310, a stopper driving apparatus 350 mounted on an upper surface of the plate 310, and a stopper 320 that is provided on an upper portion of the stopper driving apparatus 350 so as to be vertically movable.

Any number of position determining holes 170 may be formed in the disc 10, provided that the number of position determining holes 170 corresponds to the number of detection zones 141, 142, and 143.

In order to stop the disc 10 at a desired position, the stopper 320 is inserted into the position determining hole 170 that corresponds to the desired detection zone.

As illustrated on FIG. 17, the slider 30 moves along the radial direction of the disc 10. As the slider 30 is moved, the slider 30 moves to a portion at which the desired position determining groove of the position determining grooves 151, 152, and 153 is positioned.

As illustrated in FIG. 18, as the slider 30 moves into position, the stopper 320 is extended by the stopper driving apparatus 350, and is inserted into the appropriate one of the position determining grooves 151, 152, and 153, thereby stopping the disc 10 from rotating.

When rotation of the disc 10 is stopped, the lighting apparatus 51 radiates light onto the detection zones 141, 142, and 143, and the reaction result is provided in the form of data by using the light that is received from the detection zones 141, 142, and 143 by the optical sensing apparatus 52.

Although a few exemplary embodiments have been shown and described, it would be appreciated by those skilled in the art that changes may be made in these embodiments without departing from the principles and spirit of the disclosure, the scope of which is defined in the claims and their equivalents.

What is claimed is:

1. A sample analysis apparatus comprising:
   a disc configured to rotate on a rotation shaft and having at least one detection zone;
   an optical sensing apparatus configured to detect a reaction result at the at least one detection zone;
   at least one position determining protrusion provided on an exterior surface of the disc at a position corresponding to the at least one detection zone;
   a slider disposed so as to be movable in a radial direction relative to the disc; and
   a stopper mounted to the slider, and configured to stop rotation of the disc by blocking a rotational path of and contacting the at least one position determining protrusion.

2. The sample analysis apparatus of claim 1, wherein:
the stopper is configured to stop the rotation of the disc at a position where the optical sensing apparatus is able to detect the at least one detection zone.

3. The sample analysis apparatus of claim 1, wherein:
the disc comprises a first position determining protrusion located a first distance from the rotational shaft in a radial direction, and a second position determining protrusion located a second distance from the rotational shaft in a radial direction.

4. The sample analysis apparatus of claim 3, wherein:
the at least one detection domain comprises a first detection zone corresponding to the first position determining protrusion and a second detection zone corresponding to the second position determining protrusion.

5. The sample analysis apparatus of claim 4, wherein:
when the stopper stops the rotation of the disc by blocking the rotational path of the first position determining protrusion, the first detection zone is stopped at a position where the optical sensing apparatus is able to detect the first detection zone.

6. The sample analysis apparatus of claim 4, wherein:
when the stopper stops the rotation of the disc by blocking the rotational path of the second position determining protrusion, the second detection zone is stopped at a position where the optical sensing apparatus is able to detect the second detection zone.

7. The sample analysis apparatus of claim 3, wherein:
the slider is configured to move between the rotation shaft and an outer periphery of the disc.

8. The sample analysis apparatus of claim 1, wherein:
the stopper comprises a securing portion configured to secure the at least one position determining protrusion.

9. The sample analysis apparatus of claim 1, wherein:
the stopper comprises a cushion member disposed on a surface thereof that contacts the position determining protrusion.

10. The sample analysis apparatus of claim 1, wherein:
the stopper comprises a grip unit configured to stop the position determining protrusion by pressing the position determining protrusion from opposite directions.

11. The sample analysis apparatus of claim 1, wherein:
the slider comprises a stop detection unit configured to detect whether the position determining portion is stopped by the stopper.

12. The sample analysis apparatus of claim 11, wherein:
the stop detection unit comprises a hinged stopper and is configured to determine whether the position determining protrusion is stopped by detecting movement of the hinged stopper.

13. The sample analysis apparatus of claim 11, wherein:
the stop detection unit comprises a switch.

14. The sample analysis apparatus of claim 1, wherein:
the slider comprises a position detection unit configured to detect whether the stopper is moved to a position capable of stopping the position determining protrusion.

15. The sample analysis apparatus of claim 14, wherein:
the position detection unit comprises a light emitting portion, and a light receiving portion disposed opposite one another and such that the position determining protrusion will pass therebetween.

16. The sample analysis apparatus of claim 1, wherein:
the optical sensing apparatus is mounted to the slider.

17. The sample analysis apparatus of claim 1, wherein:
the optical sensing apparatus comprises a camera module configured to photograph the at least one detection zone.

18. A sample analysis apparatus comprising:
a disc configured to rotate on a rotation shaft and having at least one detection zone;
an optical sensor configured to detect the at least one detection zone;
at least one position determining protrusion provided on an exterior surface of the disc at a position corresponding to the at least one detection zone; and
a slider disposed to move between a rotational center of the disc and a external edge of the disc in a radial direction, and configured to block and contact the position determining protrusion to stop the disc at a desired position.

* * * * *